United States Patent
Pirazzoli et al.

(10) Patent No.: US 7,186,342 B2
(45) Date of Patent: Mar. 6, 2007

(54) METHOD FOR FILLING AND WASHING A FILTER FOR A DIALYSIS MACHINE

(75) Inventors: Paolo Pirazzoli, San Prospero (IT); Paolo Rovatti, Finale Emilia (IT)

(73) Assignee: Gambro Lundia AB, Lund (SE)

( * ) Notice: Subject to any disclaimer, the term of this patent is extended or adjusted under 35 U.S.C. 154(b) by 361 days.

(21) Appl. No.: 10/479,797

(22) PCT Filed: May 16, 2002

(86) PCT No.: PCT/IB02/01774

§ 371 (c)(1),
(2), (4) Date: Dec. 5, 2003

(87) PCT Pub. No.: WO02/098491

PCT Pub. Date: Dec. 12, 2002

(65) Prior Publication Data

US 2004/0149656 A1    Aug. 5, 2004

(30) Foreign Application Priority Data

Jun. 5, 2001 (IT) .......................... BO2001A0354

(51) Int. Cl.
- *B01D 61/30* (2006.01)
- *B01D 61/26* (2006.01)
- *B01D 61/28* (2006.01)
- *B01D 61/32* (2006.01)
- *A61M 1/14* (2006.01)

(52) U.S. Cl. .................. 210/636; 210/252; 210/258; 210/321.65; 210/321.71; 210/645; 210/646; 210/650; 210/739; 210/741; 210/805; 604/4.01; 604/5.01; 604/6.09; 604/6.11

(58) Field of Classification Search ................ 210/252, 210/257.2, 258, 321.65, 321.71, 645, 646, 210/647, 650, 739, 741, 805, 929, 636; 604/4.01, 604/5.01, 6.09, 6.11
See application file for complete search history.

(56) References Cited

U.S. PATENT DOCUMENTS 5,259,961 A * 11/1993 Eigendorf .................... 210/646

(Continued)

FOREIGN PATENT DOCUMENTS

DE           3442744 C2      6/1986

(Continued)

OTHER PUBLICATIONS

Taku, N. et al., "Dialysis System and Cleaning and Priming Method Thereof", Abstract of European Patent No. EP0992255, (Apr. 12, 2000).

(Continued)

*Primary Examiner*—John Kim
(74) *Attorney, Agent, or Firm*—Finnegan, Henderson, Farabow, Garrett & Dunner, L.L.P.

(57) ABSTRACT

A dialysis machine is provided with a dialysate circuit, a blood circuit and a filter having a dialysate compartment connected to the dialysate circuit, a blood compartment connected to the blood circuit, and a semi-permeable membrane to separate the dialysate compartment from the blood compartment. A method for filling and washing the filter includes the recirculation of a physiological saline in the dialysate circuit and the transfer of the physiological saline from the dialysate circuit to the blood circuit through the semi-permeable membrane.

36 Claims, 1 Drawing Sheet

U.S. PATENT DOCUMENTS

| | | | |
|---|---|---|---|
| 5,702,606 A * | 12/1997 | Peter et al. | 210/646 |
| 5,730,730 A * | 3/1998 | Darling, Jr. | 604/246 |
| 6,132,616 A | 10/2000 | Twardowski et al. | |
| 6,277,272 B1 * | 8/2001 | Nikaido et al. | 210/97 |
| 6,331,252 B1 * | 12/2001 | El Sayyid et al. | 210/646 |
| 6,582,604 B2 * | 6/2003 | Nikaido et al. | 210/636 |

FOREIGN PATENT DOCUMENTS

| | | |
|---|---|---|
| EP | 0 560 368 B1 | 9/1993 |
| JP | 1-113064 | 5/1989 |
| JP | 3-254755 | 11/1991 |
| JP | 8-150201 | 6/1996 |
| JP | 9-028791 | 2/1997 |

OTHER PUBLICATIONS

Hans-Guenther, E., "Device for On-Line Cleaning and Filling of an Extracorporal Blood Circuit of a Dialysis Apparatus", Abstract of European Patent No. EP0720856, (Jul. 10, 1996).

Scot, C. C. et al., "Methods and Apparatus for Performing controlled Ultrafiltration During Hemodialysis", Abstract of WIPO No. WO0006217, (Feb. 10, 2000).

* cited by examiner

METHOD FOR FILLING AND WASHING A FILTER FOR A DIALYSIS MACHINE

FIELD OF THE INVENTION

The present invention relates to a method for filling and washing a filter for a dialysis machine.

BACKGROUND OF THE INVENTION

A dialysis machine of the known type generally comprises a blood circulation circuit, a dialysate circulation circuit and a filter, which is provided with a dialysate compartment, a blood compartment and a semi-permeable membrane to separate the dialysate compartment from the blood compartment. The dialysate compartment is connected to the dialysate circuit, while the blood compartment is connected to the blood circuit, in such a way that the blood to be treated and the dialysate, generally flowing in opposite directions, pass through the blood compartment and the dialysate compartment respectively during the dialysis treatment.

During the dialysis treatment, unwanted particles contained in the blood migrate from the blood compartment to the dialysate compartment through the semi-permeable membrane both by diffusion and by convection, as a result of the passage of some of the liquid contained in the blood towards the dialysate compartment. Thus the patient will have lost some weight by the end of the dialysis treatment.

In operation, the blood circuit is connected to the patient's cardiovascular system to collect the blood to be treated and return the treated blood to the patient, and comprises a venous branch and an arterial branch, which is partially wrapped around a lobed rotor to form a peristaltic blood circulation pump.

Before the dialysis treatment is started, the filter must be filled by an operation generally called "priming", and the filter must then be washed in order to eliminate air bubbles, which may be formed in the initial stage of circulating a liquid through the filter, and preservatives which are used to sterilize the filter and the blood circuit. According to the known methods of filter washing, the blood circuit is made into a closed loop, a bag of physiological saline is connected to a branch of the blood circuit, and the physiological saline is recirculated in the blood circuit.

BRIEF SUMMARY OF THE INVENTION

The object of the present invention is to provide a method of filling-and-washing the filter of a dialysis machine which is simple, economical and requires minimum intervention by the operator.

According to the present invention, a method of filling and washing the filter of a dialysis machine is provided, the machine comprising a dialysate circuit, a blood circuit and a filter comprising a dialysate compartment connected to the dialysate circuit, a blood compartment connected to the blood circuit, and a semi-permeable membrane to separate the dialysate compartment from the blood compartment; the method comprising the recirculation of a physiological saline in the said dialysate circuit in such a way that the dialysate compartment is filled and washed with the said physiological saline; the method being characterized in that some of the said physiological saline is transferred from the dialysate compartment to the blood compartment through the said semi-permeable membrane.

By transferring the physiological saline through the semi-permeable membrane, it is possible to dispense with the bag of physiological saline, which is normally used for filling and washing the blood compartment of the filter. The filling and washing of the blood compartment of the filter are simplified because they do not require special components such as the bag of physiological saline. Consequently the operator's workload is also reduced. Furthermore, the transfer of some of the physiological saline through the membrane makes it possible to carry out a particularly thorough wash.

The physiological saline is transferred from the dialysate compartment to the blood compartment as a result of a pressure difference between the dialysate compartment and the blood compartment, so that some of the physiological saline is transferred from the dialysate compartment to the blood compartment through the semi-permeable membrane.

DETAILED DESCRIPTION

Figure 1:
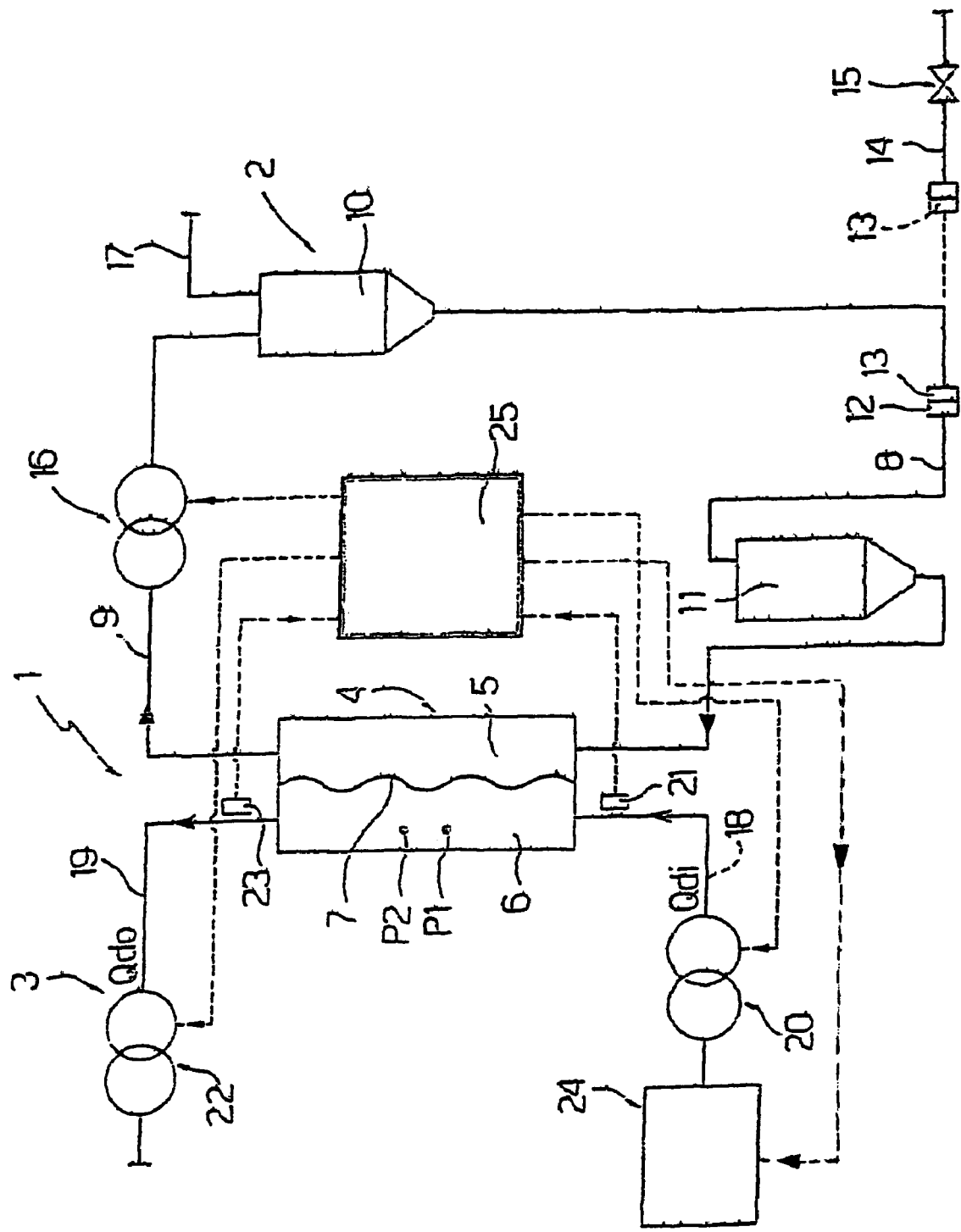
FIG. 1 is a schematic view of a dialysis machine of a preferred embodiment of the present invention.

To enable the present invention to be understood more clearly, a preferred embodiment will now be described, purely by way of example and without restrictive intent, with reference to the attached FIGURE, which is a schematic view of a dialysis machine, with parts removed for clarity.

In the attached FIGURE, the number 1 indicates the whole of a dialysis machine, which comprises a blood circuit 2, a dialysate circuit 3 and a filter 4, which is provided with a blood compartment 5 and a dialysate compartment 6 separated by a semi-permeable membrane 7, an arterial branch 8 connected to the compartment 5, a venous branch 9 connected to the compartment 5, a dropper 10 located in the venous branch 9 and a dropper 11 located in the arterial branch.

The branches 8 and 9 have at their ends connectors 12 and 13 respectively, which can be connected by a connection device (not illustrated) to a patient, and which, in the attached FIGURE, are connected to each other. The venous branch 9 can be connected, by the connector 13, to a branch 14, in which a valve 15 is fitted. In the attached FIGURE, one portion of the venous branch 9 is shown in broken lines in the configuration in which it is connected to the branch 14.

The venous branch 9 is wrapped around a rotor of a peristaltic pump 16 up-line from the dropper 10, which is provided with a vent tube 17.

The circuit 3 comprises a branch 18 connected to the compartment 6 to supply the dialysate to the filter 4, and a branch 19 connected to the compartment to remove the dialysate and the impurities transferred through the membrane 7 by the filter 4. Along the branch 18 there are located a pump 20 providing a flow rate $Q_{di}$ of dialysate to the inlet of the filter 4, and a pressure sensor 21 located between the pump 20 and the filter 4, and along the branch 19 there are located a pump 22 providing a rate of flow $Q_{do}$ of dialysate from the outlet of the filter 4, and a pressure sensor 23 located between the filter 4 and the pump 22. The branch 18 is connected to a device 24, which supplies the dialysate as a solution of salts in purified water according to methods known in the field of dialysis treatment. In addition to supplying the physiological saline solution, the device 24 is configured to prepare the physiological saline solution from salts and purified water.

The machine 1 comprises a control unit 25, which is connected to the pumps 16, 20 and 22, to the sensors 21 and 23 and to the device 24, and, in practice, is capable of controlling the operation of the machine 1 during the dialysis treatment and the operations of washing the filter 4.

With specific reference to the filling and washing of the filter 4, the attached FIGURE shows the circuit 2 in a loop configuration, in other words with the connectors 12 and 13 connected to each other. In this configuration, the circuit 2 and the filter are empty; in other words, they contain air at atmospheric pressure. The control unit 25 is designed to wash the filter 4 in a filling and washing cycle, which comprises the steps of operating the pumps 20 and 22 to fill the compartment 6 with dialysate, in other words with a physiological saline supplied by the device 24. In this step the pumps 20 and 22 are operated in such a way as to produce a pressure P1 in the compartment 6 of the filter 4. When the compartment 6 has been filled, the pumps 20 and 22 are operated in such a way as to produce a pressure P2 in the compartment 6. The pumps 20 and 22 are of the positive displacement type, and therefore the pressure in the portion lying between the two pumps 20 and 22, and consequently in the compartment 6, can be varied by operating the two pumps 20 and 22. The pumps 20 and 22 are regulated by the control unit 25, which processes the pressure signals received by the sensors 21 and 23 and has a knowledge of the atmospheric pressure, and can produce, by means of the pumps 20 and 22, a pressure difference between the compartment 6 and the compartment 5 such that the physiological saline is transferred from the compartment 6 to the compartment 5. Some of the dialysate contained in the compartment 6 at the pressure P2 passes through the semi-permeable membrane 7 and progressively fills the compartment 5 of the filter 4 and the circuit 2. The membrane 7 has the characteristic of being semi-permeable and of allowing the liquid to flow when there is a pressure difference between the compartment 6 and the compartment 5. The flow of liquid through the membrane 7 increases as the pressure difference between the compartment 6 and the compartment 5 increases. The pressure in the compartment 5 is equal to atmospheric pressure, since the blood circuit 2 is connected to the exterior through the vent tube 17. During the filling of the circuit 2, the peristaltic pump 16 is operated to circulate the physiological saline in the circuit 2 which is in a closed loop configuration, while the air contained in the circuit 2 is progressively discharged through the vent tube 17. The physiological saline is circulated through the circuit 2 for a specified period, in order to eliminate the air bubbles and the preservative substances used to sterilize the filter 4, in other words in order to wash the filter 4. On completion of the washing, the circuit 2 is opened and the connector 12 is connected to the patient, while the connector 13 (shown in broken lines in the attached FIGURE) is connected to the branch 14. The dialysis treatment is then started, according to the characteristic procedures and operating parameters for the patient. In the initial stage of the dialysis treatment, the valve 15 is open so that the physiological saline used for washing the filter 4 is discharged through the branch 14, while in the circuit 2 the patient's blood progressively replaces the physiological saline. When the blood reaches the branch 14, the valve 15 is closed and the connector is connected to the patient. In the meantime, the device 24 supplies the dialysate to the circuit 3 in a solution whose concentration is determined by the control unit 25.

The invention claimed is:

1. A method of filling and washing a filter of a dialysis machine, comprising the steps of:
providing a dialysis machine having:
  a filter comprising a dialysate compartment, a blood compartment, and a semi-permeable membrane to separate the dialysate compartment from the blood compartment;
  a blood circuit comprising an arterial branch connected to the blood compartment, a venous branch connected to the blood compartment, a first dropper located in the arterial branch, a second dropper located in the venous branch, and a vent tube connected to one of said first and second droppers,
  a peristaltic pump connected to the blood circuit;
  a dialysate circuit comprising a first branch connected to the dialysate compartment to supply a fresh dialysate to the filter and a second branch connected to the dialysate compartment to remove a spent dialysate from the filter;
  a first pump located along the first branch to provide a flow rate of fresh dialysate to an inlet of the filter;
  a first pressure sensor located along the first branch between the first pump and the filter;
  a second pump located along the second branch to provide a flow rate of spent dialysate from an outlet of the filter;
  a second pressure sensor located along the second branch between the filter and the second pump;
  a supplying device connected to the first branch for supplying a fresh dialysate for a dialysis treatment as a solution of salts in purified water, and
  a control unit connected to the first pump, the second pump, the peristaltic pump, the first pressure sensor, the second pressure sensor, and the supplying device;
configuring the blood circuit to form a loop connected by said vent tube to the exterior of the blood circuit, whereby the pressure in the blood compartment is equal to the atmospheric pressure;
operating the first pump and the second pump to fill and wash the dialysate compartment with a priming liquid at a first pressure, the priming liquid being supplied by said supplying device;
when the dialysate compartment has been filled and washed with the priming liquid, operating the first pump and the second pump to supply the dialysate compartment with the priming liquid at a second pressure, the second pressure being greater than the first pressure and greater than atmospheric pressure, and the second pressure defining a pressure difference between the dialysate compartment and the blood compartment such that the priming liquid is transferred from the dialysate compartment to the blood compartment through the semi-permeable membrane, during said transfer, the control unit receiving information related to a pressure in the blood circuit in said loop, and the control unit processing pressure signals supplied by said first and second pressure sensors to regulate said first and second pumps;
operating the peristaltic pump to circulate said priming liquid in the blood circuit in said loop, and
discharging air contained in the blood circuit in said loop through the vent tube.

2. A method according to claim 1, wherein said priming liquid is a physiological saline solution prepared by said supplying device from salts and purified water.

3. A method of filling and washing a filter of a dialysis machine, comprising the steps of:
providing a dialysis machine having:

a filter comprising a dialysate compartment, a blood compartment, and a semi-permeable membrane to separate the dialysate compartment from the blood compartment;

a blood circuit comprising an arterial branch connected to the blood compartment, a venous branch connected to the blood compartment, an arterial chamber located in the arterial branch, and a venous chamber located in the venous branch;

a dialysate circuit comprising a first branch connected to the dialysate compartment to supply a fresh dialysate to the filter and a second branch connected to the dialysate compartment to remove a spent dialysate from the filter;

a first pump located along the first branch to provide a flow rate of fresh dialysate to an inlet of the filter;

a first pressure sensor located along the first branch between the first pump and the filter;

a second pump located along the second branch to provide a flow rate of spent dialysate from an outlet of the filter;

a second pressure sensor located along the second branch between the filter and the second pump; and a control unit connected to the first pump, the second pump, the first pressure sensor, and the second pressure sensor; and operating the first pump and the second pump to supply the dialysate compartment with a priming liquid at a first pressure defining a pressure difference between the dialysate compartment and the blood compartment such that the priming liquid is transferred from the dialysate compartment to the blood compartment through the semi-permeable membrane, during said transfer, the control unit processing pressure signals supplied by the first pressure sensor and the second pressure sensor to regulate the first pump and the second pump.

4. A method according to claim 3, further comprising the step of operating the first pump and the second pump to fill and wash the dialysate compartment with the priming liquid at a second pressure, the first pressure being greater than the second pressure.

5. A method according to claim 3, wherein the dialysis machine further has a supplying device connected to the first branch for supplying a fresh dialysate for a dialysis treatment as a solution of salts in purified water, said priming liquid being supplied by said supplying device.

6. A method according to claim 5, wherein said priming liquid is a physiological saline solution formed by said supplying device from said salts and said purified water.

7. A method according to claim 3, wherein said blood circuit further comprises a vent tube connected to one of said arterial and venous chambers.

8. A method according to claim 7, further comprising the step of discharging air contained in the blood circuit through the vent tube.

9. A method according to claim 3, wherein the blood circuit is configured to form a loop connected by a vent tube to an exterior of the blood circuit.

10. A method according to claim 3, wherein during said step of operating the first pump and the second pump to supply the dialysate compartment with a priming liquid at a first pressure, a pressure in the blood compartment is equal to an atmospheric pressure, and said first pressure is greater than the atmospheric pressure.

11. A method according to claim 3, wherein during said step of operating the first pump and the second pump to supply the dialysate compartment with a priming liquid at a first pressure, the control unit receives information related to a pressure in the blood circuit.

12. A method according to claim 3, wherein the dialysis machine is provided with a peristaltic pump connected to the blood circuit, the method further comprising a step of operating said peristaltic pump to circulate said priming liquid in the blood circuit.

13. A method of operating a dialysis machine, comprising the steps of providing a dialysis machine having:
a filter comprising a dialysate compartment, a blood compartment, and a semi-permeable membrane to separate the dialysate compartment from the blood compartment;
a blood circuit connected to the blood compartment;
a dialysate circuit comprising a first branch connected to the dialysate compartment to supply a fresh dialysate to the filter and a second branch connected to the dialysate compartment to remove a spent dialysate from the filter;
a supplying device configured to supply the first branch with a fresh dialysate for a dialysis treatment, said supplying device being configured to form a physiological saline solution from salts and purified water and to supply the first branch with said physiological saline solution; and
a control unit connected to said supplying device; operating said supplying device to prepare the physiological saline solution from said salts and said purified water;

supplying the dialysate compartment with said physiological saline solution at a first pressure defining a pressure difference between the dialysate compartment and the blood compartment such that said physiological saline solution is transferred from the dialysate compartment through the semi-permeable membrane to the blood compartment to fill and wash the blood compartment; and connecting the blood circuit to a patient and starting a dialysis treatment, during the dialysis treatment, said supplying device being operated to supply the first branch with a fresh dialysate for the dialysis treatment.

14. A method according to claim 13, further comprising the step of supplying the dialysate compartment with said physiological saline solution at a second pressure to fill and wash the dialysate compartment, said first pressure being greater than said second pressure.

15. A method according to claim 13, wherein the step of starting a dialysis treatment comprises supplying the blood circuit with a patient—s blood whereby the blood replaces the physiological saline solution, and discharging the physiological saline solution through a branch connected to the blood circuit.

16. A method according to claim 13, wherein during the filling and washing of the blood compartment, the blood circuit is connected by a vent tube to the exterior of the blood circuit, whereby a pressure in the blood compartment is equal to an atmospheric pressure, said first pressure of the physiological saline solution being greater than the atmospheric pressure.

17. A method according to claim 13, further comprising the steps of circulating the physiological saline solution in the blood circuit, and discharging air contained in the blood circuit through a vent tube.

18. A method according to claim 13, wherein:
a first pump is located along the first branch;

a first pressure sensor is located along the first branch between the first pump and the filter;
a second pump is located along the second branch;
a second pressure sensor is located along the second branch between the filter and the second pump;
the control unit is connected to the first pump, the second pump, the first pressure sensor, and the second pressure sensor; and
during the filling and washing of the blood compartment with the physiological saline solution, the first pump and the second pump are operated to produce said first pressure.

19. A method according to claim 13, wherein during the filling and washing of the blood compartment with the physiological saline solution, a peristaltic pump is connected to the blood circuit and is operated to circulate the physiological saline solution in the blood circuit.

20. A method according to claim 19, wherein during the operation of the peristaltic pump, the blood circuit is closed to form a loop.

21. A dialysis machine comprising:
a filter comprising a dialysate compartment, a blood compartment, and a semi-permeable membrane to separate the dialysate compartment from the blood compartment;
a blood circuit comprising an arterial branch connected to the blood compartment, a venous branch connected to the blood compartment, an arterial chamber located in the arterial branch, and a venous chamber located in the venous branch;
a dialysate circuit comprising a first branch connected to the dialysate compartment to supply a fresh dialysate to the filter and a second branch connected to the dialysate compartment to remove a spent dialysate from the filter;
a first pump located along the first branch to provide a flow rate of fresh dialysate to an inlet of the filter;
a first pressure sensor located along the first branch between the first pump and the filter;
a second pump located along the second branch to provide a flow rate of spent dialysate from an outlet of the filter;
a second pressure sensor located along the second branch between the filter and the second pump;
a control unit connected to the first pump, the second pump, the first pressure sensor, and the second pressure sensor, said control unit being designed to operate the first pump and the second pump to supply the dialysate compartment with a priming liquid at a first pressure defining a pressure difference between the dialysate compartment and the blood compartment such that the priming liquid is transferred from the dialysate compartment to the blood compartment through the semi-permeable membrane, during said transfer, the control unit processing pressure signals supplied by the first pressure sensor and the second pressure sensor to regulate the first pump and the second pump.

22. A dialysis machine according to claim 21, wherein the control unit is designed to operate the first pump and the second pump to fill and wash the dialysate compartment with the priming liquid at a second pressure, the first pressure being greater than the second pressure.

23. A dialysis machine according to claim 21, further comprising a supplying device connected to the first branch for supplying a fresh dialysate for a dialysis treatment as a solution of salts in purified water, the control unit being connected to the supplying device and designed to operate said supplying device to supply said priming liquid.

24. A dialysis machine according to claim 23, wherein said supplying device is configured to form a physiological saline solution from said salts and said purified water, said priming liquid being a physiological saline solution formed by said supplying device from salts and purified water.

25. A dialysis machine according to claim 21, wherein said blood circuit further comprises a vent tube connected to one of said arterial and venous chambers.

26. A dialysis machine according to claim 21, wherein said blood circuit is configured to form a loop connected to an exterior of the blood circuit through a vent tube.

27. A dialysis machine according to claim 21, wherein during said step of supplying the priming liquid at a first pressure, the control unit receives information related to a pressure in the blood circuit.

28. A dialysis machine according to claim 21, further comprising a peristaltic pump connected to the blood circuit, said control unit being connected to the peristaltic pump and designed to operate said peristaltic pump to circulate said priming liquid in the blood circuit.

29. A dialysis machine comprising:
a filter comprising a dialysate compartment, a blood compartment, and a semi-permeable membrane to separate the dialysate compartment from the blood compartment;
a blood circuit connected to the blood compartment;
a dialysate circuit comprising a first branch connected to the dialysate compartment to supply a fresh dialysate to the filter and a second branch connected to the dialysate compartment to remove a spent dialysate from the filter;
a supplying device designed for supplying the first branch with a fresh dialysate for a dialysis treatment, said supplying device being configured to form a physiological saline solution from salts and purified water and to supply the first branch with said physiological saline solution; and
a control unit connected to said supplying device and designed to carry out the following steps:
forming the physiological saline solution from said salts and said purified water and supplying the first branch with said physiological saline solution;
supplying the dialysate compartment with said physiological saline solution at a first pressure defining a pressure difference between the dialysate compartment and the blood compartment such that said physiological saline solution is transferred from the dialysate compartment through the semi-permeable membrane to the blood compartment to fill and wash the blood compartment; and
during a dialysis treatment, supplying the first branch with a fresh dialysate for the dialysis treatment.

30. A dialysis machine according to claim 29, wherein the control unit is designed to carry out the step of supplying the dialysate compartment with said physiological saline solution at a second pressure to fill and wash the dialysate compartment, said first pressure being greater than said second pressure.

31. A dialysis machine according to claim 29, comprising a discharging branch connected to the blood circuit for discharging the physiological saline solution.

32. A dialysis machine according to claim 29, comprising a vent tube for connecting the blood circuit to an exterior of the blood circuit whereby a pressure in the blood compartment is equal to the atmospheric pressure, said first pressure of the physiological saline solution being greater than atmospheric pressure.

33. A dialysis machine according to claim 29, further comprising a vent tube for discharging air contained in the blood circuit.

34. A dialysis machine according to claim 29, wherein the dialysis circuit comprises:
- a first pump located along the first branch;
- a first pressure sensor located along the first branch between the first pump and the filter;
- a second pump located along the second branch; and
- a second pressure sensor located along the second branch between the filter and the second pump;
- the control unit being connected to the first pump, the second pump, the first pressure sensor, and the second pressure sensor, the control unit being designed to operate the first pump and the second pump to produce said first pressure.

35. A dialysis machine according to claim 29, further comprising a peristaltic pump connected to the blood circuit, said control unit being connected to the peristaltic pump and designed to operate said peristaltic pump to circulate said physiological saline solution in the blood circuit.

36. A dialysis machine according to claim 35, wherein the blood circuit is closed to form a loop.

* * * * *

UNITED STATES PATENT AND TRADEMARK OFFICE
CERTIFICATE OF CORRECTION

| | | |
|---|---|---|
| PATENT NO. | : 7,186,342 B2 | Page 1 of 1 |
| APPLICATION NO. | : 10/479797 | |
| DATED | : March 6, 2007 | |
| INVENTOR(S) | : Pirazzoli et al. | |

It is certified that error appears in the above-identified patent and that said Letters Patent is hereby corrected as shown below:

Claim 15, col. 6, line 51, "patient–s" should read --patient's--.

Signed and Sealed this

First Day of May, 2007

JON W. DUDAS
*Director of the United States Patent and Trademark Office*